(12) United States Patent
Solanki et al.

(10) Patent No.: US 6,182,661 B1
(45) Date of Patent: Feb. 6, 2001

(54) CONDOMS

(75) Inventors: Suren Solanki, Huntington; Janette Louise Rodgers, Ketton, both of (GB)

(73) Assignee: LRC Products Limited, Herts (GB)

( * ) Notice: Under 35 U.S.C. 154(b), the term of this patent shall be extended for 0 days.

(21) Appl. No.: 09/355,190

(22) PCT Filed: Jan. 29, 1998

(86) PCT No.: PCT/GB98/00279

§ 371 Date: Aug. 13, 1999

§ 102(e) Date: Aug. 13, 1999

(87) PCT Pub. No.: WO98/33459

PCT Pub. Date: Aug. 6, 1998

(30) Foreign Application Priority Data

Jan. 31, 1997 (GB) ................................................. 9702019

(51) Int. Cl.⁷ .......................................................... A61F 6/04
(52) U.S. Cl. ............................................ 128/844; 128/918
(58) Field of Search ................................. 128/842, 844, 128/918; 604/347–353

(56) References Cited

U.S. PATENT DOCUMENTS

| 2,586,674 | * | 2/1952 | Lonne | 128/844 |
| 3,809,090 | * | 5/1974 | Povlacs | 128/294 |
| 4,329,312 | | 5/1982 | Ganz . | |
| 4,852,586 | | 8/1989 | Haines . | |

FOREIGN PATENT DOCUMENTS

| 1400332 | 7/1975 | (GB) . |
| 89/07428 | 8/1989 | (WO) . |
| 91/06268 | 5/1991 | (WO) . |
| 94/20052 | 9/1994 | (WO) . |

* cited by examiner

Primary Examiner—Michael A. Brown
(74) Attorney, Agent, or Firm—Dykema Gossett PLLC

(57) ABSTRACT

A method of manufacturing a condom having an open end and a closed end, wherein the method is comprised of the steps of coating a former, applying material, in addition to the coating material, to areas of the former thereby creating monolithic stimulation projections between the ends of the condom.

The method further includes the steps of coating the former after the stimulation projections have been formed, applying the additional material in a continuous stream or in a series of discrete pulses by a dispensing gun and rotating the former during the application of the additional material.

13 Claims, 4 Drawing Sheets

CONDOMS

This invention relates to condoms, and it is particularly concerned with condoms intended to be worn on the penis during sexual intercourse to reduce the risks of unwanted pregnancy or infection.

By using a grooved mandrel on which condoms are manufactured by a dip moulding process, it is known to produce condoms with ribs which are claimed to heighten female stimulation during coitus. However, the ribs on such condoms produced by the known method are not effectively positioned or lack sufficient structural rigidity to produce effective clitoral and labial stimulation, and the production of pronounced ribbing by shaping of the mandrel weakens the structural integrity of the condom which is plainly unacceptable.

The present invention addresses the deficiencies of the known method of manufacturing condoms designed to promote stimulation of the clitoris, and it resides in a method of manufacturing a condom having an open end and a closed end, the method comprising the step of coating a former, and as a separate step, selectively applying material additional to the coating material to areas of the former to form stimulation means between the ends of the completed condom.

The simulation means may comprise one or more monolithic projections. The or each projection may have a predetermined configuration defined by the selective application of the additional material.

The condom of the invention is preferably manufactured by a multi-dip moulding process in which a conventionally shaped former is dipped into successive liquid baths, e.g. of latex, liquid polyurethane or another synthetic polymer, and the stimulation means are applied between dips. Alternatively, the stimulation means could be secured to an otherwise completed condom.

The additional material may be applied by dispensing means in a continuous stream or in a series of discrete pulses. Preferably the dispensing means comprise one or more dispensing guns. The former may be rotated about its longitudinal axis during application of the additional material, and additionally the dispensing means can be moved along the longitudinal axis of the former at the same time.

The invention also provides a condom manufactured in accordance with the method.

Furthermore, in accordance with the invention there is provided a condom comprising a body having a closed end and an open end, and stimulation means between the ends of the condom for clitoral and labial stimulation, the stimulation means comprising one or more firm projections.

The additional material can be a thickened latex formulation, a heat-sensitive latex formulation, a silicone rubber or another suitable polymeric material.

The projections are defined by a local increase in thickness of the condom material and preferably they comprise a harder material than the remainder of the body enabling projections to be obtained by directly applying the material in a viscous fluid state. According to one embodiment of the invention the stimulation means comprise a plurality of domelike studs, which may be arranged in a regular circumferential array. In another embodiment, the stimulation means comprises an elongate helical ridge.

The protrusion or protrusions massage and stimulate the clitoris during coitus and can serve as a visual and tactile indication that the condom is correctly oriented on the penis before and during intercourse.

The stimulation means may span a distance of between 30 mm and 100 mm along the condom, and preferably they span a distance of approximately 70 mm.

A clear understanding of the invention will be gained from the following detailed description of some particular embodiments, given with reference to the accompanying drawings, in which:

FIG. 2 is an enlarged side view of the open end of the condom shown in FIG. 1a;

FIG. 4 is a partial enlarged side view of the condom shown in FIG. 3a; and

Figure 1A:
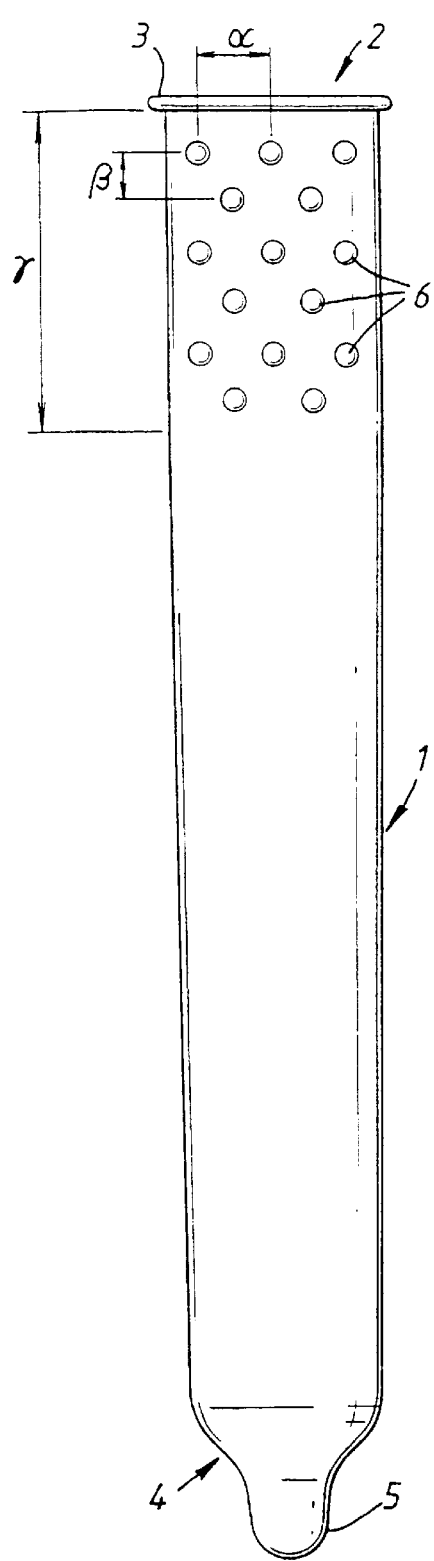
FIG. 1a and 1b are side views of different condoms embodying the invention.

The condoms illustrated in FIGS. 1 and 3 are of a generally conventional configuration. A cylindrical membrane 1 has an open end 2 provided with a conventional ring 3 which serves to retain the condom on the penis during coitus. The other end 4 of the membrane 1 is closed, and it has a centrally located bell-shaped nipple or teat 5.

Figure 1B:
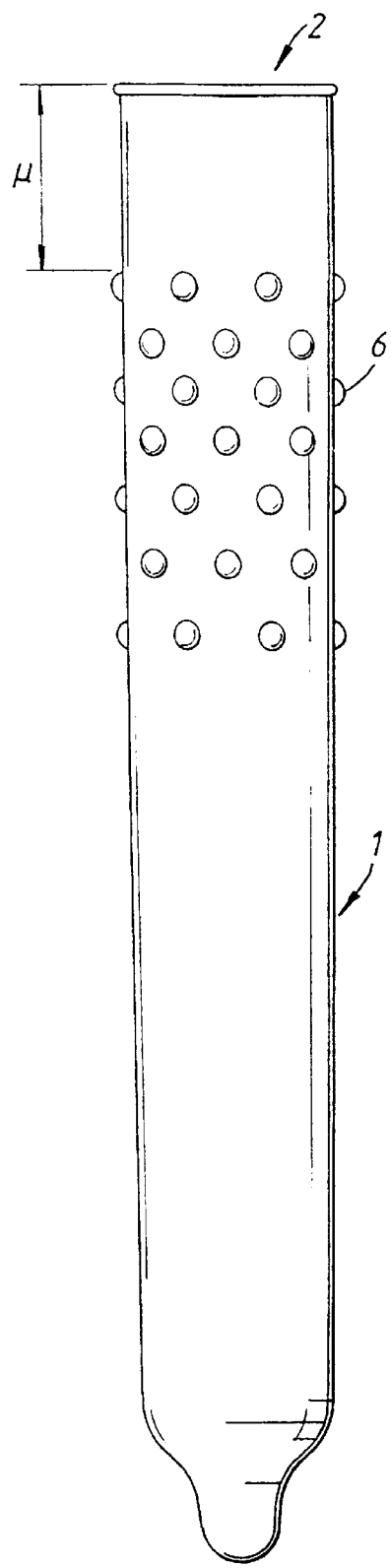
Figure 2:
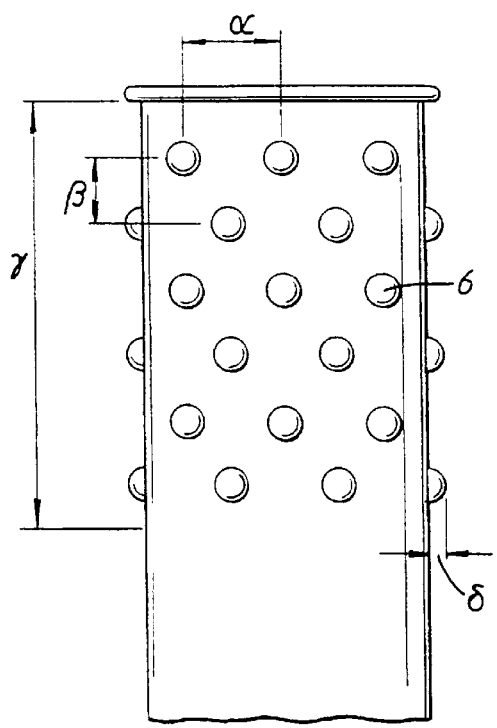

The condom of FIGS. 1 and 2 has a plurality of domelike studs, pips or knobbles 6 arranged in a regular circumferential array in the region of the open end of the condom, and confined to a minor part of the condom length. The studded area may be located immediately adjacent the open end of the condom, but in the preferred embodiment shown in FIG. 1b a distance $\mu$ of between 30 mm and 50 mm is devoid of studs. As shown the studs are arranged in six circumferential rows of studs with the studs in each row equally spaced apart at a distance $\alpha$ in the range of 10 mm to 20 mm, e.g. at 15 mm. The rows are spaced apart along the condom at a constant pitch $\beta$ in the range of 5 mm to 15 mm, preferably about 10 mm. Adjacent rows of studs 6 are circumferentially offset by half the distance between adjacent studs in the same row. It will be appreciated that different numbers of studs per row and different numbers of rows are possible. For example the number of rows could be as few as three or as many as ten. Also the studs could be arranged in different arrays, either regular or irregular.

In the preferred embodiment the studs 6 have a basal diameter of 5 mm and a height $\delta$ of 1.5 mm. However, the basal diameter and the height of the studs could be in the range of 2 mm to 7 mm and 0.5 mm to 3 mm respectively, and the same condom can be provided with studs of different sizes. Preferably the height of the stud is in the range of 1 mm to 2.5 mm.

Figure 3A:
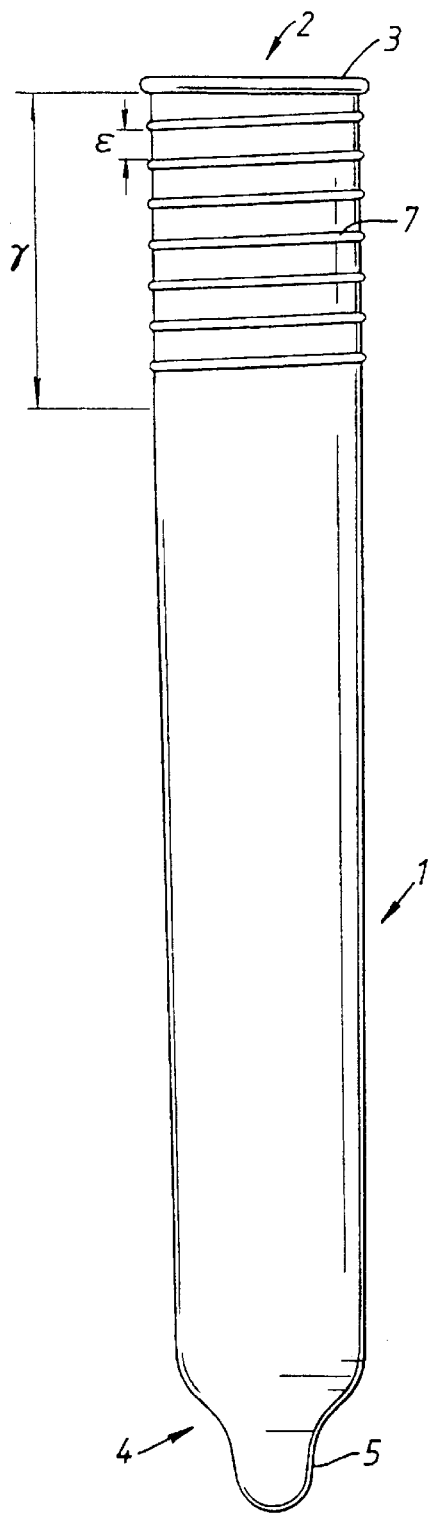
FIGS. 3a and 3b are side views of a further condoms embodying the invention.
Figure 3B:
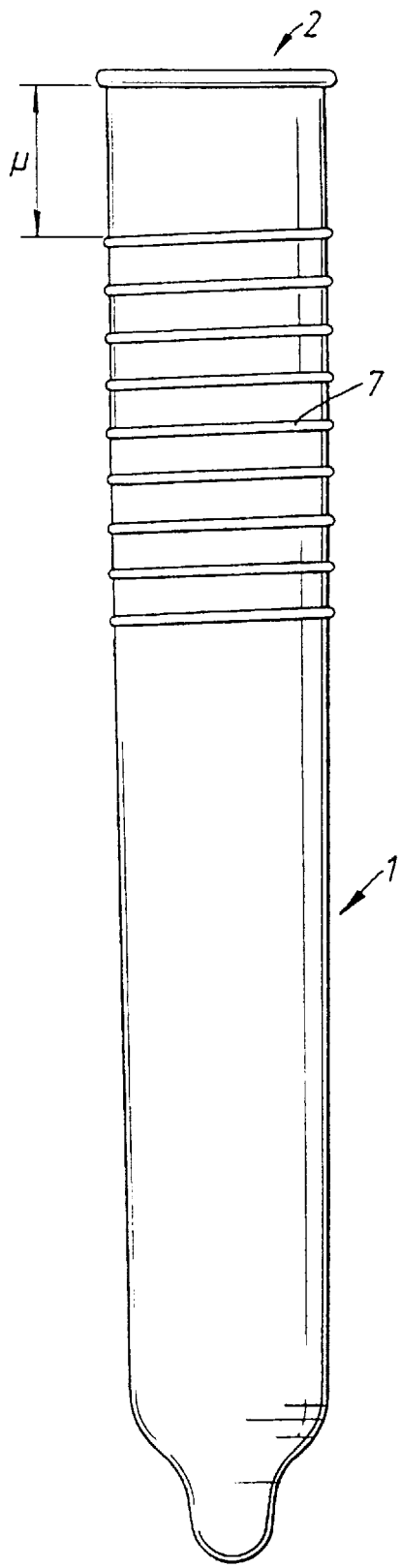
Figure 4:
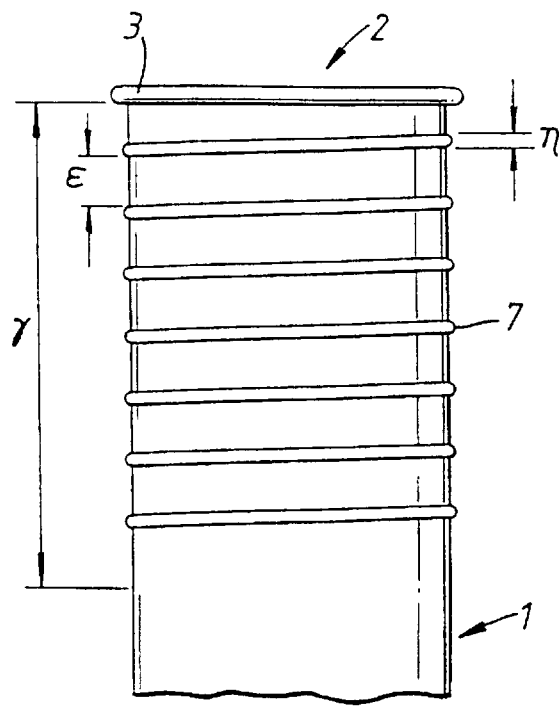

The condom of FIGS. 3 and 4 has a single helical ridge 7 commencing in the region of the open end 2. The pitch $\epsilon$ of the ridge 7 can be between 5 mm and 15 mm, and preferably it is 10 mm. The helical ridge makes a plurality of turns about the condom, e.g. from 3 to 10 turns, and preferably about seven turns as shown. The riddle 7 has a width $\eta$ within the range of 0.5 mm to 1.5 mm preferably about 1 mm, and it has a rounded profile to avoid sharp edges. The height of the ridge is preferably 0.5 to 1 times the ridge width. The ridge can be conveniently formed by applying a cylindrical bead of viscous material, or it can be preformed. The start of the ridge is preferably located a distance $\mu$ from the open end (FIG. 3b) but the ridge may start immediately adjacent the open end (FIG. 3a).

In the described embodiments, the studs 6 or the ridge 7 may span a length $\gamma$ in the range of 30 mm to 100 mm, but a span lengthwise of 70 mm is preferred. Whilst the studs and helical ridge have been described as alternative embodiments, they could be incorporated in the same condom. if desired. The remainder of the condom is devoid of studs or ridges.

The thickness of the membrane 1 is preferably less than 0.10 mm, and the thickness of a medium weight condom typically is around 0.07 mm. However, the membrane may have a thickness of 0.04 mm or less. Thinner condom membranes are preferred because they enhance tactility and heat transfer. The ratio of protrusion height to membrane thickness is greater than 5 to 1 and it is preferably between 10 to 1 and 30 to 1.

Figure 5:
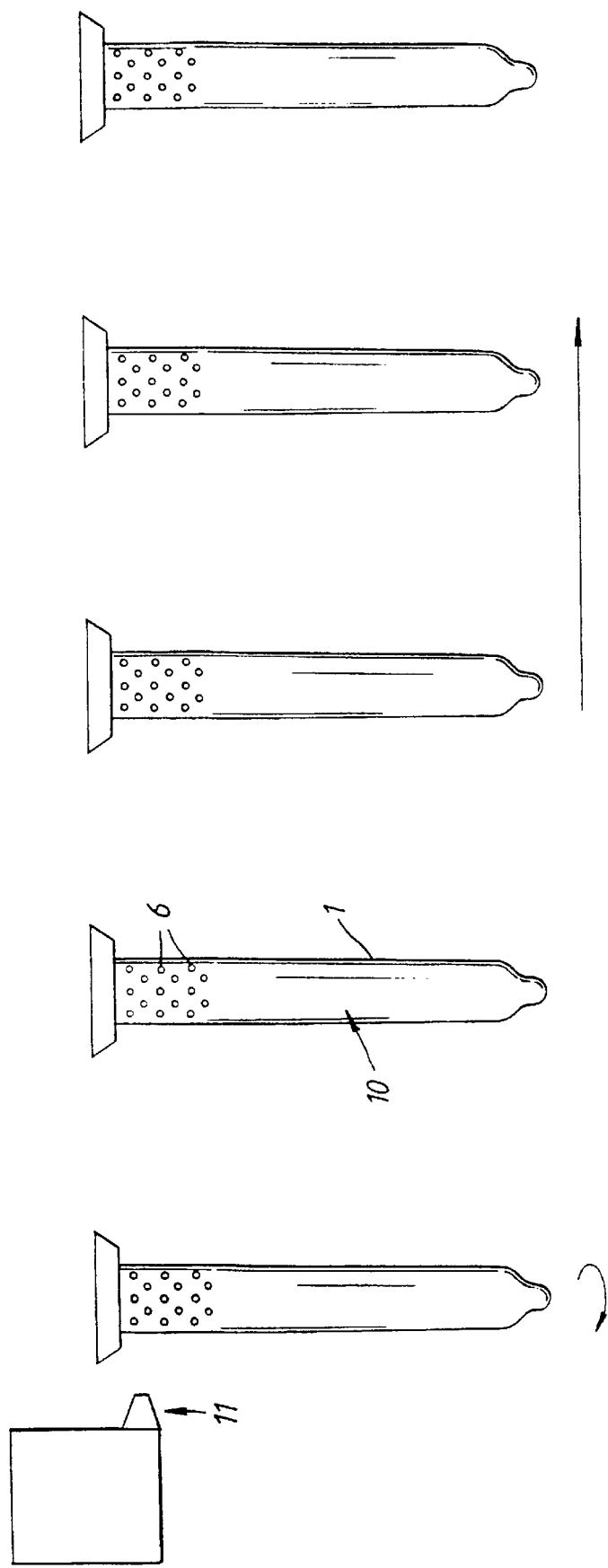
FIG. 5 is a schematic illustration of the condom of FIGS. 1 and 2 during manufacture.

FIG. 5 depicts a schematic illustration of the preferred method of manufacturing the condom of the invention. The condoms are manufactured by a dip moulding process in which a conventionally shaped former or mandrel 10 is dipped into successive liquid baths, e.g. two baths of latex or liquid polyurethane. Between dips the former 10 is rotated about its longitudinal axis and a relatively viscous material, e.g. thickened latex, is applied by a dispensing gun 11 either in bursts to produce the studs 6 or continuously to form the ridge 7, the gun being advanced along the mandrel as required. When the mandrel is subsequently dipped into a further liquid bath the studs 6 or ridge 7 are overmoulded and are held between layers of the condom material. When set, the viscous material is harder than the material forming the body of the condom, and thus the hardened material retains its shape and provides a firm protrusion for effective clitoral stimulation. More than one dispensing gun may be utilised to expedite the application of the thicker material. The gun may also be placed after the second dip and before final vulcanisation.

Depending on the form and height of the protrusions forming the stimulation means, there is the possibility that their presence may impede the donning of the rolled condom. It has been found that in many cases the protrusions do not hinder donning when the condom is of the conventional type having a substantially constant diameter over essentially the whole of its length. However, in cases where there is a danger that the protrusions may impede donning, the diameter of the condom may be between 5% and 15% greater at the open end than the diameter adjacent the closed end and preferably the diameter is approximately 10% greater. The condom may be tapered uniformly from the closed end to the open end, or it can be flared from a position between the two ends. Alternatively, the condom may be tapered from the closed end to a position adjacent the start of studs or the ridge, with the remaining length of the condom being generally cylindrical.

Modifications to the described embodiments are of course possible without departing from the scope of the invention. For instance, a plurality of axial or oblique ridges, a series of spaced circumferential ridges, or more than one helical ridge, could be applied in place of the single helical ridge. Also a combination of ridges and studs could be used. However, the described embodiments are prefelted because they are easier to apply than other formations.

What is claimed is:

1. A method for manufacturing a condom having an open end and a closed end, the method comprising the steps of coating a former, and as a separate step, selectively applying additional material to the coating material to areas of the former to form stimulation means between the ends of the completed condom.

2. A method according to claim 1, wherein a further coating is applied to the former after the stimulation means has been applied.

3. A method according to claim 1, wherein the additional material is applied in a continuous stream by dispensing means.

4. A method according to claim 3, wherein the dispensing means comprise one or more dispensing guns.

5. A method according to claim 3, wherein the dispensing means is moved relative to the longitudinal axis of the former during the application of additional material.

6. A method according to claim 1, wherein the additional material is applied in a series of discrete pulses by dispensing means.

7. A method according to claim 1, wherein the former is rotated about its longitudinal axis during the application of the additional material.

8. A method according to claim 1, wherein the additional material comprises at least one of thickened latex, a heat-sensitive latex formulation, a silicone rubber, and polymeric material.

9. A method according to claim 1, wherein the former is coated by spraying material onto the former.

10. A method according to claim 1, wherein the additional material has a higher modulus of elasticity that the coating material.

11. A condom manufactured by the method of claim 1.

12. A condom comprising:
a body having a closed end and an open end;
stimulation means between the ends of the condom for clitoral and labial stimulation, the stimulation means comprising at least one firm projection;
wherein the region of the closed end is substantially devoid of projections, and the at least one firm projection is monolithic and has a height of between 0.5 mm and 3 mm.

13. A condom comprising:
a body having a closed end and an open end;
stimulation means between the ends of the condom for clitoral and labial stimulation, the stimulation means comprising at least one firm projection;
wherein the material forming the at least one firm projection has a higher modulus of elasticity than the material forming the body.

* * * * *